(12) United States Patent
Roh et al.

(10) Patent No.: US 11,357,582 B1
(45) Date of Patent: Jun. 14, 2022

(54) SYSTEM FOR TRANSCRIBING AND PERFORMING ANALYSIS ON PATIENT DATA

(71) Applicant: IX Innovation LLC, Seattle, WA (US)

(72) Inventors: Jeffrey Roh, Seattle, WA (US); Justin Esterberg, Mercer Island, WA (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/568,442

(22) Filed: Jan. 4, 2022

(51) Int. Cl.
| | |
|---|---|
| *A61B 17/00* | (2006.01) |
| *A61B 34/00* | (2016.01) |
| *G16H 50/20* | (2018.01) |
| *G16H 50/50* | (2018.01) |
| *G10L 15/22* | (2006.01) |
| *G10L 15/26* | (2006.01) |
| *G10L 15/30* | (2013.01) |
| *G10L 13/02* | (2013.01) |
| *G10L 15/06* | (2013.01) |
| *G06V 10/40* | (2022.01) |
| *G06T 7/00* | (2017.01) |
| *G16B 20/20* | (2019.01) |
| *G16B 40/20* | (2019.01) |
| *G16H 10/60* | (2018.01) |

(52) U.S. Cl.
CPC ............ *A61B 34/25* (2016.02); *G06T 7/0012* (2013.01); *G06V 10/40* (2022.01); *G10L 13/02* (2013.01); *G10L 15/063* (2013.01); *G10L 15/22* (2013.01); *G10L 15/26* (2013.01); *G10L 15/30* (2013.01); *G16B 20/20* (2019.02); *G16B 40/20* (2019.02); *G16H 10/60* (2018.01); *G16H 50/20* (2018.01); *G16H 50/50* (2018.01); *A61B 2034/256* (2016.02); *G06T 2207/30004* (2013.01); *G06V 2201/03* (2022.01)

(58) Field of Classification Search
CPC . A61B 34/25; A61B 2034/256; G06T 7/0012; G06T 2207/30004; G06V 10/40; G06V 2201/03; G10L 13/02; G10L 15/063; G10L 15/22; G10L 15/26; G10L 15/30; G16B 20/20; G16B 40/20; G16H 10/60; G16H 50/20; G16H 50/50
USPC .............................................. 606/1; 705/2, 3
See application file for complete search history.

(56) References Cited

U.S. PATENT DOCUMENTS

| | | | |
|---|---|---|---|
| 10,565,977 B1 * | 2/2020 | Miller .............. | G10K 11/17823 |
| 2008/0235057 A1 * | 9/2008 | Weidenhaupt ......... | G16H 50/20 705/3 |
| 2012/0053957 A1 * | 3/2012 | Atkins ................... | G16H 50/30 705/2 |

(Continued)

*Primary Examiner* — Charlotte M Baker
(74) *Attorney, Agent, or Firm* — Perkins Coie LLP

(57) ABSTRACT

Methods, apparatuses, and systems for transcribing and performing analysis on patient data are disclosed. Data is collected from one or more medical professionals as well as sensors and imaging devices positioned on or oriented towards a patient. An analysis is performed on the patient data and the data is presented to a medical professional via a verbal interface in a conversational manner, allowing the medical professional to provide additional data such as observations or instructions which may be used for further analysis or to perform actions related to the patient's care.

19 Claims, 10 Drawing Sheets

(56) References Cited

U.S. PATENT DOCUMENTS

| | | | | |
|---|---|---|---|---|
| 2019/0348178 A1* | 11/2019 | Eleftherou | ............. | G16H 10/60 |
| 2021/0166812 A1* | 6/2021 | Amir | .................... | A61B 5/0053 |
| 2021/0241246 A1* | 8/2021 | Liberti | .................. | G06Q 10/20 |
| 2021/0398666 A1* | 12/2021 | Maslik | ................. | A61B 5/4842 |

* cited by examiner

| Date | Patient ID | Image File | Heart Rate | SpO2 | Blood Pressure | Diagnosis |
|---|---|---|---|---|---|---|
| 1/7/2020 | 67546 | 67546_MRI01 | 90 | 98 | 130/85 | Healthy |
| 2/23/2020 | 67546 | N/A | 95 | 98 | 125/85 | Healthy |
| 6/28/2020 | 67546 | 67546_MRI02 | 90 | 96 | 130/90 | Pneumonia |
| 7/17/2020 | 67546 | N/A | 100 | 97 | 140/85 | Healthy |
| 12/20/2020 | 67546 | 67546_MRI03 | 110 | 95 | 135/90 | Lung Cancer |
| 1/26/2021 | 67546 | N/A | 105 | 95 | 140/90 | Lung Cancer |
| 6/30/2021 | 67546 | 67546_MRI04 | 120 | 94 | 145/95 | Lung Cancer |

*FIG. 7*

SYSTEM FOR TRANSCRIBING AND PERFORMING ANALYSIS ON PATIENT DATA

TECHNICAL FIELD

The present disclosure is generally related to automated and robotic surgical procedures and specifically to systems and methods for transcribing and performing analysis on patient data.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure as well as technical surgical errors during the operation. For example, adverse events can occur due to (i) breakdown in communication within and among the surgical team, care providers, patients, and their families; (ii) delay in diagnosis or failure to diagnose; and (iii) delay in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the healthcare team. However, conventional methods are typically insufficient to prevent surgical errors and adverse events during surgery.

BRIEF DESCRIPTION OF THE DRAWINGS

FIG. 7 is a table illustrating an example patient database, in accordance with one or more embodiments.

DETAILED DESCRIPTION

Figure 1:
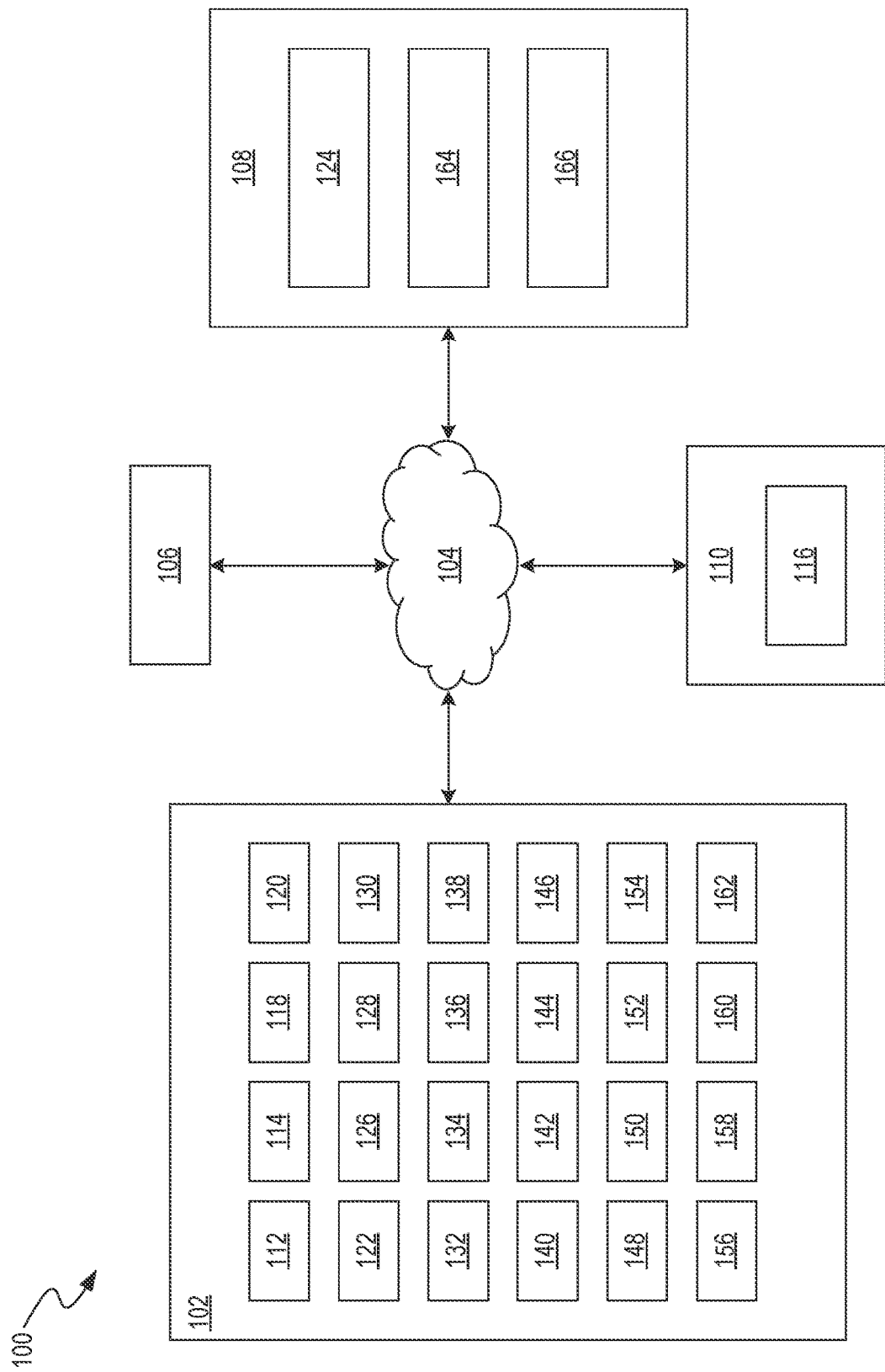
FIG. 1 is a block diagram illustrating an example system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "602") can implement components, operations, or structures (e.g., "602a") described as a single instance. Further, plural instances (e.g., "602") refer collectively to a set of components, operations, or structures (e.g., "602a") described as a single instance. The description of a single component (e.g., "602a") applies equally to a like-numbered component (e.g., "602b") unless indicated otherwise. These and other aspects, features, and implementations can be expressed as methods, apparatuses, systems, components, program products, means or steps for performing a function, and in other ways. These and other aspects, features, and implementations will become apparent from the following descriptions including the claims.

Medical transcription is a resource intensive process which can additionally consume a large amount of a healthcare provider's time, however, thorough documentation is critical to the long-term care of a patient and ensures the continuity of care when multiple care providers are involved in a patient's care. Quickly and accurately documenting this data can facilitate rapid coordination of patient care, however, this is commonly performed by manual transcription. Beyond recording data, a medical professional, such as a physician, surgeon, imaging technician, pathologist, etc., must analyze the data and make observations ultimately culminating in a diagnosis. This analysis may be computer aided; however, the observations are largely subjective. This results in a large degree of variability in assessments and diagnoses, not to mention time spent manually reviewing data collected about the patient.

The embodiments disclosed herein describe methods, apparatuses, and systems for transcribing and performing analysis on patient data. In some embodiments, data is collected from one or more medical professionals as well as sensors and imaging devices positioned on or oriented towards a patient. An analysis is performed on the patient data and the data is presented to a medical professional via a user interface in a conversational manner, allowing the medical professional to provide additional data such as observations or instructions which may be used for further analysis or to perform actions related to the patient's care.

The advantages and benefits of the methods, systems, and apparatuses disclosed herein include compatibility with best practice guidelines for performing surgery in an operating room, e.g., from regulatory bodies and professional standards organizations such as the Association for Surgical Technologists. The embodiments disclosed provide the ability to analyze data and recognize patterns with greater consistency than humans. Furthermore, the methods disclosed can be implemented in a range of processing capabilities, ranging from simple silicon-based consumer-grade computers, to commercial cloud computers and large-scale supercomputers, to newly developed quantum computers. Each of these implementations represents an increase in scale of computing resources that could be utilized to perform a deeper analysis in a similar amount of time that cannot be matched by a human. The embodiments disclosed improve and automate the transcription process and assist in the analysis of patient data. Thus, a surgeon or other medical professional can decrease the amount of time needed reviewing such data to arrive at a diagnosis, or in the case of a surgeon, planning a surgical procedure. The embodiments result in prompter interventions which may be consequential in more favorable patient outcomes. Similarly, the systems disclosed enable medical professionals to be more efficient allowing them to address the needs of more patients in the same amount of time.

The robotic surgery technologies disclosed further offer valuable enhancements to medical or surgical processes through improved precision, stability, and dexterity. The disclosed methods relieve medical personnel from routine tasks and make medical procedures safer and less costly for patients. The embodiments disclosed enable performing more accurate surgery in more minute locations on or within the human body. The embodiments also address the use of dangerous substances. The adoption of robotic systems, according to the embodiments disclosed herein, provides several additional benefits, including efficiency and speed improvements, lower costs, and higher accuracy. The equipment tracking system integrated into the disclosed embodiments offers flexibility and other advantages, such as requiring no line-of-sight, reading multiple radio frequency identification (RFID) objects at once, and scanning at a distance. The advantages offered by the surgical tower according to the embodiments disclosed herein are smaller incisions, less pain, lower risk of infection, shorter hospital stays, quicker recovery time, less scarring, and reduced blood loss. The advantages of the convolutional neural network (CNN) used for machine learning (ML) in the disclosed embodiments include the obviation of feature extraction and the use of shared weight in convolutional layers, which means that the same filter (weights bank) is used for each node in the layer; this both reduces memory footprint and improves performance.

FIG. 1 is a block diagram illustrating an example system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility, such as a hospital, the doctor's office 110, or outpatient surgery center.

In some embodiments, the system 100 includes one or more medical or surgical patient monitors 112. The monitors 112 can include a vital signs monitor (a medical diagnostic instrument), which can be a portable, battery powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiologic parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end-tidal CO2 monitor or capnography monitor used for measurement of the level of carbon dioxide that is released at the end of an exhaled breath (referred to as end-tidal carbon dioxide, ETCO2). An end-tidal CO2 monitor or capnography monitor is widely used in anesthesia and intensive care. ETCO2 can be computed by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end-tidal CO2 monitor can be configured as side stream (diverting) or mainstream (non-diverting). A diverting end-tidal CO2 monitor transports a portion of a patient's respired gases from the sampling site to the end-tidal CO2 monitor while a non-diverting end-tidal CO2 monitor does not transport gas away. Also, measurement by the end-tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in artery, used in the operating room 102) for measurement. The non-invasive method (referred to as a sphygmomanometer) works by measurement of force exerted against arterial walls during ventricular systole (i.e., systolic blood pressure occurs when the heart beats and pushes blood through the arteries) and ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate, which is the rate at which breathing occurs, and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can bring a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia where the heart rate becomes faster and bradycardia where the heart rate becomes slower), coronary heart disease, heart attacks, or cardiomyopathy. The instrument used for measurement of the electrocardiogram is called an electrocardiograph which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which help in guiding the surgeon during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP), the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG), the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation, and does not perform external stimulation. Spontaneous EMG is recorded by the insertion of a needle electrode. Triggered EMG refers to the recording of myoelectric signals during stimulation of a target site such as pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgeon or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by performing a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. The doctor moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgeon makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals over long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles which allow the surgeon to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engages with one another. When a telescope is used to operate on the abdomen, the procedure is called laparoscopy. The surgical tower 128 typically includes access to a variety of surgical tools, such as, for example, electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles) which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument can 130 consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools and minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool-tissue interaction forces. During MIS, the field of view and workspace of surgical tools are compromised due to the indirect access to the anatomy and lack of surgeon's hand-eye coordination. The sensors 134 provide a tactile sensation to the surgeon by providing information of shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used can be brain/spinal cord anomalies, tumors in the body, breast cancer screening, joint injuries, uterine/pelvic pain detection, or heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI can more widely suit for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer which produces sound waves and sends them into the body. The sound waves that are reflected are converted into electrical signals which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for the fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgeons in the placement of specialized surgical instruments and implants. The patient images are taken to guide the physician before or during the medical procedure. The stereotactic navigation system 138 includes a camera having infrared sensors to determine the location of the tip of the probe being used in the surgical procedure. This information is sent in real-time so that the surgeons have a clear image of the precise location where they are working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a post-operative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table which is designed for use in spinal surgeries and can be used in a variety of spinal procedures in supine, prone, or lateral positions in a safe manner. Two peculiar features of the Jackson table 144 are no central table support and an ability to rotate the table through 180 degrees. The Jackson table 144 is supported at both ends which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets which cover the patient. The blanket can be designed to use pressure points on the patient's body to prevent heat from reaching areas at risk for pressure sores or burns. The blanket can also include drain holes where fluid passes through the surface of the blanket to linen underneath which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors which can contribute to poor quality in the environment of the operating room 102 are temperature, ventilation, and humidity, and those conditions can lead to profound effects on the health and work productivity of people in the operating room 102. As an example: surgeons prefer a cool, dry climate since they work in bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter. High-Efficiency Particulate Air filter (HEPA filter) protects from infection and contamination by a filter which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system which controls the muscles). A major percentage of orthopedic tools are made of plastic. The orthopedic tools can be divided into the following specialties: hand and wrist, foot and ankle, shoulder and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be of type absorbable (the stitches automatically break down harmlessly in the body over time without intervention) and non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as sensor/transducer, signal conditioner, display, data storage unit, etc. In some embodiments, the medical equipment includes a sensor to receive a signal from a measurand/patient; a transducer for converting one form of energy to electrical energy; a signal conditioner such as an amplifier, filter, etc., to convert the output from the transducer into an electrical value; a display to provide a visual representation of the measured parameter or quantity; and a storage system to store data which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allows it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment. The consumables 158 can include gloves, gowns, masks, syringes, needles, sutures, staples, tubing, catheters, or adhesives for wound dressing, in addition to other surgical tools needed by doctors and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries are performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR are a digital version of patients' paper charts. The EHR database 106 can contain more information than a traditional patient chart, including, but not limited to, a patients' medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

Figure 2:
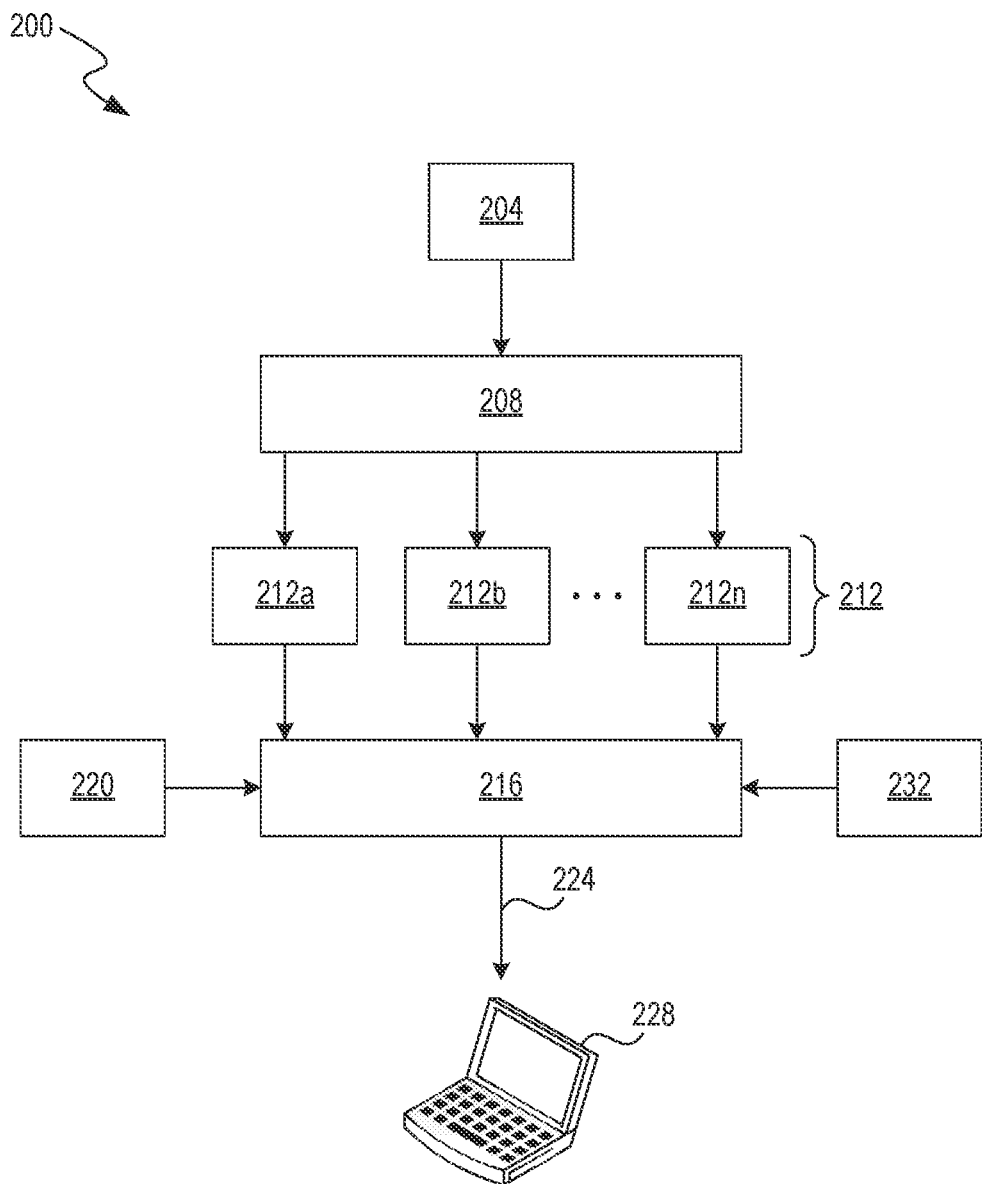
FIG. 2 is a block diagram illustrating an example machine learning (ML) system, in accordance with one or more embodiments.

FIG. 2 is a block diagram illustrating an example machine learning (ML) system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . , 212n. The feature extraction module 208 reduces the redundancy in the input data 204, e.g., repetitive data values, to transform the input data 204 into the reduced set of features 212, e.g., features 212a, 212b, . . . , 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place.

Figure 3:
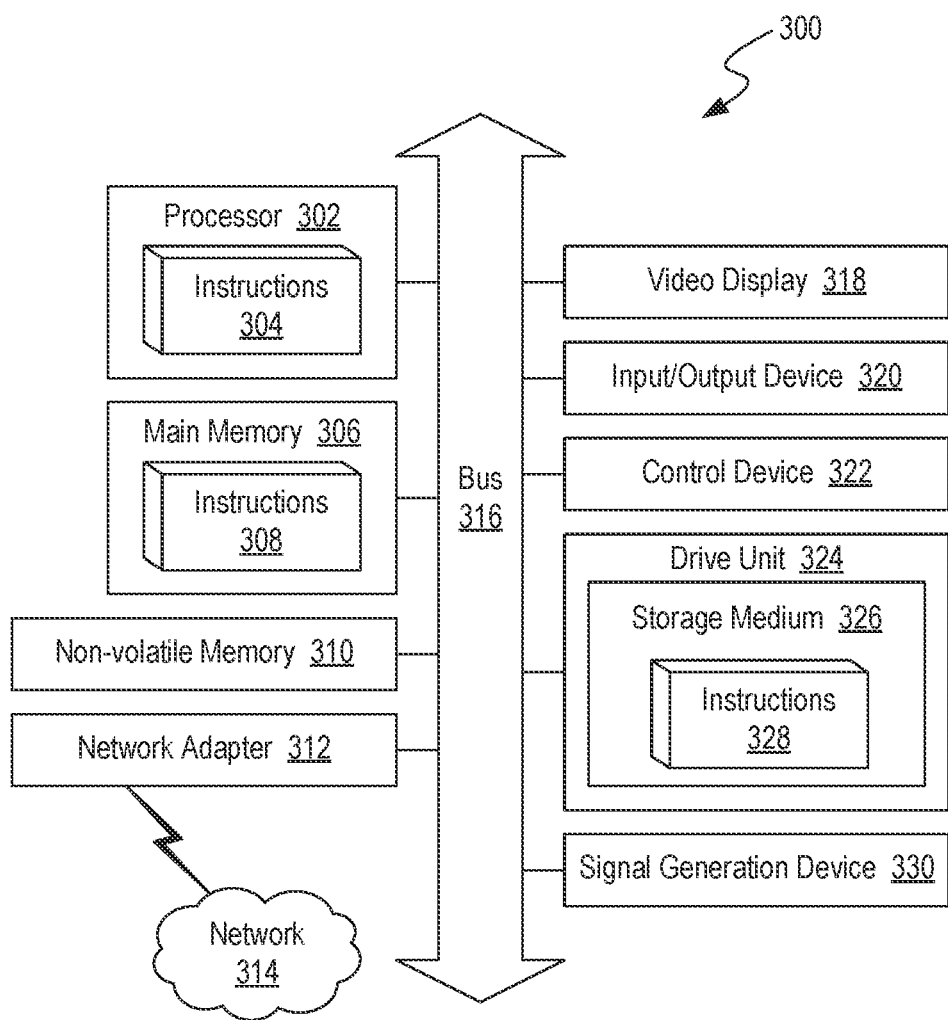
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multilayer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
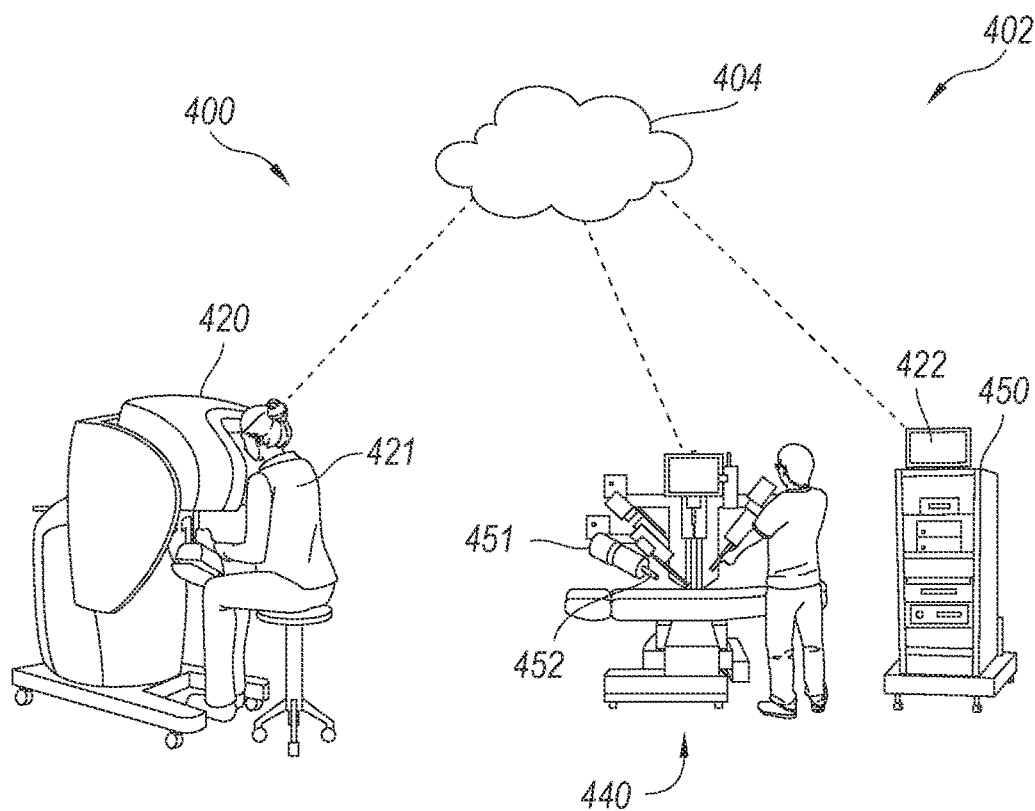
FIG. 4A is a block diagram illustrating an example robotic system, in accordance with one or more embodiments.

FIG. 4A is a block diagram illustrating an example robotic surgical system 400, in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1).

The robotic surgical system 400 includes a user device or console 420 ("console 420"), a surgical robot 440, and a computer or data system 450. The console 420 can be operated by a surgeon and can communicate with components in an operating room 402, remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc. or other features disclosed herein to perform surgical step(s) or procedures or implement steps of processes discussed herein.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to medical images, video, etc. For surgical applications, the images could include, but are not limited to, real-time optical images, real-time ultrasound, real-time OCT images and/or other modalities, or could include pre-operative images, such as MRI, CT, PET, etc. The various imaging modalities can be selectable, programmed, superimposed and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

Figure 4B:
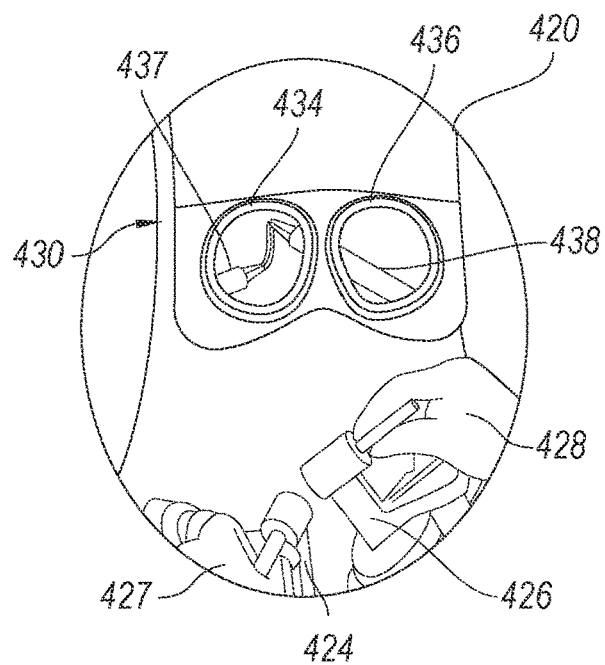
FIG. 4B illustrates an example console of the robotic system of FIG. 4A, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times.

The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452.

In an autonomous mode, the surgical robot 440 can autonomously perform steps under the control of the data system 450. The robotic surgical system 400 can be pre-programmed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include physician input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring.

In some embodiments, the robotic surgical system 400 can determine whether a detected event is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like.

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre- or post-operative virtual simulations, simulations using models, etc.) can be generated and collected.

The surgical robot 440 can include robotic arms 451 (one identified) with integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein.

The robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, Calif. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modify, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operatively or intraoperatively.

Embodiments can provide a means for mapping the surgical path for neurosurgery procedures that minimize damage through artificial intelligence mapping. The software for artificial intelligence is trained to track the least destructive pathway. The physician can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system.

Figure 5:
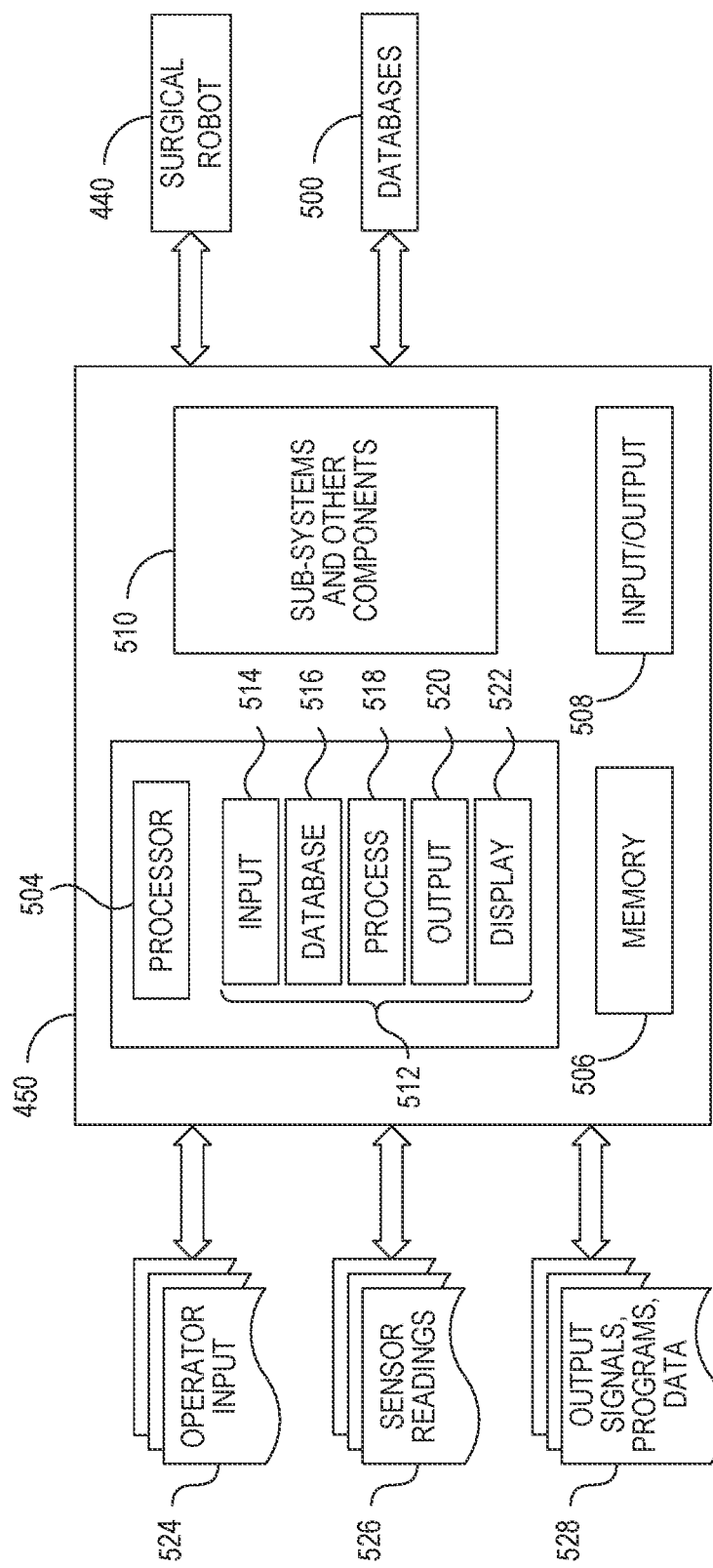
FIG. 5 is a schematic block diagram illustrating subcomponents of the robotic system of FIG. 4A, in accordance with one or more embodiments.

FIG. 5 is a schematic block diagram illustrating subcomponents of the robotic surgical system 400 of FIG. 4A in accordance with embodiment of the present technology. The data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 522 for controlling the display.

In operation, the input module 514 accepts an operator input 524 via the one or more input devices, and communicates the accepted information or selections to other components for further processing. The operator input 524 can be received via one or more keyboards, touchscreens, microphones, or other input devices. For voice input, the operator input 524 can include speech input (e.g., physician notes, observations, etc.) from the physician detected using one or more microphones. The data system 450 can perform voice processing to analyze the speech input, as discussed with reference to FIGS. 6-10 and can perform other data processing techniques disclosed herein. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field-programmable gate array, or secure application-specific integrated circuit. The memory 506 can store instructions for causing the surgical robot 440 to perform acts disclosed herein.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 500. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between surgical equipment within the surgical room. The database(s) 500 can include, without limitation, user profile databases, vocabulary databases, natural language databases, confidence score databases, training set databases, or the like. Additionally or alternatively, the databases 500 can further be accessed by transcribing modules, diagnostic modules, treatment modules, machine learning modules, or combinations thereof, which can access one or more databases.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, the output discussed in connection with FIG. 6-10, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, analysis models, patient diagnosis, observations, transcription information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

Figure 6:
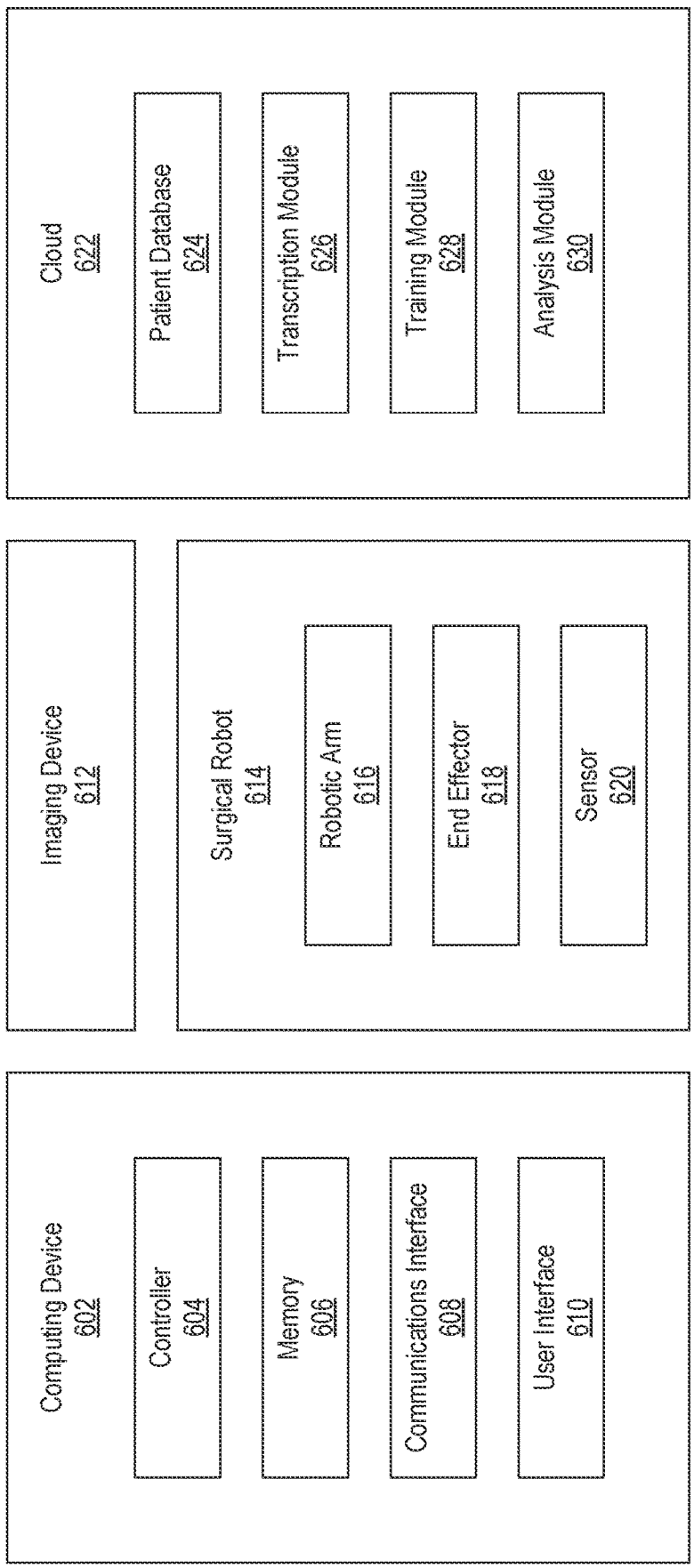
FIG. 6 is a block diagram illustrating an example system for transcribing and performing analysis on patient data, in accordance with one or more embodiments.

FIG. 6 is a block diagram illustrating an example system for transcribing and performing analysis on patient data, in accordance with one or more embodiments. The system implements a digital medical assistant. The system includes at least one computing device 602, at least one controller 604, at least one memory 606, at least one communications interface 608, and at least one user interface 610. The system is implemented using the components of the example computer system 300 illustrated and described in more detail with reference to FIG. 3. Likewise, embodiments of the system can include different and/or additional components or can be connected in different ways.

The computing device 602 (see FIG. 3) receives inputs from the user interface 610, at least one sensor 620, and at least one imaging device 612. The computing device 602 performs mathematical computations returning the results via the user interface 610, such as a display, or via speakers. The computing device 602 may additionally access the cloud 622 or other data sources via the communications interface 608. The computing device 602 may be a mobile device, which is a computing device characterized by being portable. A mobile device may include any of a mobile phone, tablet, laptop, wearable device such as a smartwatch, a portable gaming device, or a proprietary device built for a specific purpose. The computing device 602 may additionally include or communicate with a quantum computing device (see FIG. 1). The controller 604 is a logic device or processor for preforming a series of logic operations. Traditionally, the controller 604 included transistors arranged on a silicon substrate, although the controller 604 included any materials and substrates which form a logic circuit. Common logic circuit elements include OR gates, AND gates, XOR gates, NOR gates, NAND gates, etc. The controller 604 may be a microcontroller or a central processing unit (CPU) in a computer. Similarly, a graphical processing unit (GPU) may be used as the controller. The controller 604 may additionally include the logic element of a quantum computer.

The controller 604 uses logic operations to perform computations and may be in communication with the memory 606 for storing data and a communications interface 608 for sending and receiving data to and from other controllers or devices. The memory 606 is a medium for storing data. The memory 606 may be volatile memory, such as random-access memory (RAM) which is a cache used by the controller 604 for temporary storage of data for use in computations or persistent memory, such as solid-state drive (SSD), hard disk drive (HDD) or other storage devices including tape drives, flash drives, memory cards, optical drives such as compact disk (CD), digital video disk (DVD), or Blu-ray disc, or data storage on nontraditional mediums. The communications interface 608, also known as a network interface, is an interface for a device or controller to communicate with another device, controller, or network resource such as the cloud 622 server or drive.

The communications interface 608 may be wired, such as by ethernet cables or universal serial bus (USB) cables, or wireless as in Wi-Fi, Bluetooth, near field communications (NFC), 4G long-term evolution (LTE), 5G, etc. The user interface 610 is a means of interacting with and providing inputs to the computing device 602. The user interface 610 may alternatively be a means of interacting with and controlling the surgical robot 614. The user interface 610 may include any of a traditional keyboard and mouse, a joystick, gamepad, trackpad, touchscreen, etc. The user interface 610 may alternatively include a sensor 620 such as a microphone for receiving an audio input such as spoken language. The user interface 610 may alternatively include eye, facial, body, or gesture tracking using an imaging device 612. The imaging device 612 is any device capable of detecting sound or electromagnetic waves and assembling a visual representation of the detected waves. Imaging devices 612 may collect waves from any part of the electromagnetic spectrum or sounds at any range of frequencies, often as a matrix of independently acquired measurements which each represent a pixel of a two or three-dimensional image. These measurements may be taken simultaneously or in series via a scanning process or a combination of methods. Some pixels of an image produced by an imaging device may be interpolated from direct measurements representing adjacent pixels in order to increase the resolution of a generated image.

The surgical robot 614 is a robotic system designed to assist a surgeon in performing a surgical operation on a patient. The surgical robot 614 may include a controller and any of a robotic arm 614 with an end effector 618 or an imaging device 612. The surgical robot 614 may further include a user interface for accepting control inputs from a user, such as a surgeon or other medical professional and a communications interface 608 for transmitting and receiving data to and from the cloud 622 for the purpose of training an artificial intelligence operating within the surgical robot or receiving remote commands from a remote user or an artificial intelligence existing external to the surgical robot 614. The robotic arm 616 is a mechanically actuated arm or lever with at least two degrees of freedom. The robotic arm 616 will typically include at least one end effector 618 or an imaging device 612 and may include both an end effector 618 and an imaging device 612. The robotic arm 616 may additionally be capable of changing the end effector 618 to facilitate multiple functions and operation of a variety of tools.

The robotic arm 616 may be manually controlled or operated in an autonomous or semi-autonomous mode. The surgical robot 614 may have one robotic arm 616 or multiple robotic arms 616, each of which may be operated independently by one or more users or autonomous systems or a combination of users and autonomous systems. The end effector 618 is the end of the robotic arm 616 which is conducting work. The end effector 616 is typically a tool 154 (see FIG. 1) or device for interacting with a physical object and may be a surgical tool intended for acting upon or within a patient or may be a gripping device for securing a separate surgical tool to the robotic arm 616. The end effector 618 may be permanently affixed to the end of the robotic arm 616 or may be detachable allowing for a system of interchangeable end effectors 618 which may alternatively be selected and swapped by a single robotic arm or multiple robotic arms. The end effector 618 may include features such as lights or other illumination devices, surgical tools, imaging devices 612, etc.

In some embodiments, the one or more sensors 620 of the system of FIG. 6 generate sensor data from measurements of a patient's body. In some embodiments, the sensors 620 are the same as or similar to the monitors 112 (see FIG. 1). In other embodiments, a sensor 620 is an input device for measuring a physical quantity and outputting the measurements as a signal which is saved as data representing the measured physical quantity. Sensors 620 may measure a range of physical quantities such as a temperature, distance, movement, orientation, sound frequency, wavelength and intensity, wavelength and intensity of light and other electromagnetic waves, volatile gases, capacitance, resistance, induction, etc. The sensor 620 may output an analog or a digital signal. The sensor 620 may be a discrete device or embedded in another device such as a robotic arm 616, end effector 618, etc. and may be accessible to the computing device 602 or cloud 622 via the communications interface 608. Alternatively, data may be stored local to the sensor 620 which may be later accessed by a device such as the computing device 602 or the cloud 622. The sensor 620 may additionally refer to an array of sensors 620 such as an image sensor or imaging device 612 for capturing multiple measurement values simultaneous and which may be used to create multidimensional representations of the data such as images.

The cloud 622 is a distributed network of computers including servers and databases. The cloud 622 may be a private cloud where access is restricted by isolating the network such as preventing external access or by using encryption to limit access to only authorized users. Alternatively, the cloud 622 may be a public cloud where access is widely available via the internet. A public cloud may not be secured or may include limited security features. The patient database 624 stores data about one or more patients. The data may include gender, age, height, weight, previously diagnosed medical conditions, medical history, family medical history, allergies, and vital information such as baseline measurements of heart rate, blood pressure, blood oxygen saturation, and respiration rate. The data may be collected from the sensors 620 or imaging devices 612 or may alternatively be collected from medical records. In some embodiments, the patient database 624 may include patient medical records created by one or more medical professionals. The transcription module 626 calls the training module 628 to train an analysis model which is used by the analysis module to perform an analysis on patient data collected by the transcription module 626 and stored in the patient database 624. The transcription module 626 interacts with a surgeon or other medical professional to record observations and instructions from a surgeon, and then present the analysis results from the analysis module to the surgeon, preferably via a speech-based interface in a conversational manner, allowing the surgeon to dictate additional observations and instructions.

The analysis results may additionally provide insights and feedback to the surgeon prompting the surgeon to provide additional information which otherwise may have been forgotten or overlooked. The training module 628 is used to train an analysis model using historical patient data from the patient database 624. The data collected or otherwise available during a patient visit is provided and a prediction is made based upon the provided data. In some embodiments, training a machine learning model (see FIG. 2) includes monitoring live surgical procedures. The machine learning model is trained based on the live surgical procedures while the live surgical procedures are being performed. The prediction is then compared to the patient's diagnosis and the analysis model is updated based upon the result, improving the model. The updated analysis model may be stored in the patient database 624 and is available for use by the transcription module 626 and the analysis module 630. The analysis module 630 is used to collect current patient data by the transcription module 626 and retrieve historical patient data from the patient database 624 to generate insights by the analysis model trained by the training module 628. The analysis model performs an analysis on the available data which may include image analysis, or other machine learning categorizations to identify any of diagnoses, treatments, additional data which may improve accuracy of the diagnosis, etc. In some embodiments, the analysis model may additionally be used to perform a deeper analysis such as by using a supercomputer or quantum computer (see FIG. 1) to simulate the progression of a disease or a treatment in a patient.

FIG. 7 is a table illustrating an example patient database 624, in accordance with one or more embodiments. In some embodiments, one or more processors of the system of FIG. 6 retrieve patient data of a patient from the patient database 624. The patient data includes at least a medical history of the patient. The patient database 624 (see FIG. 6) stores patient data about one or more patients. The data may include gender, age, height, weight, previously diagnosed medical conditions, medical history, family medical history, allergies, medications, and vital information such as baseline measurements of heart rate, blood pressure, blood oxygen saturation, and respiration rate. The data may be collected from sensors 620 or imaging devices 612 or may be obtained from medical records or provided by medical professionals. The patient database may additionally include medical records created by one or more medical professionals. The patient database 624 is used by the transcription module 626, training module 628, and analysis module 630.

Figure 8:
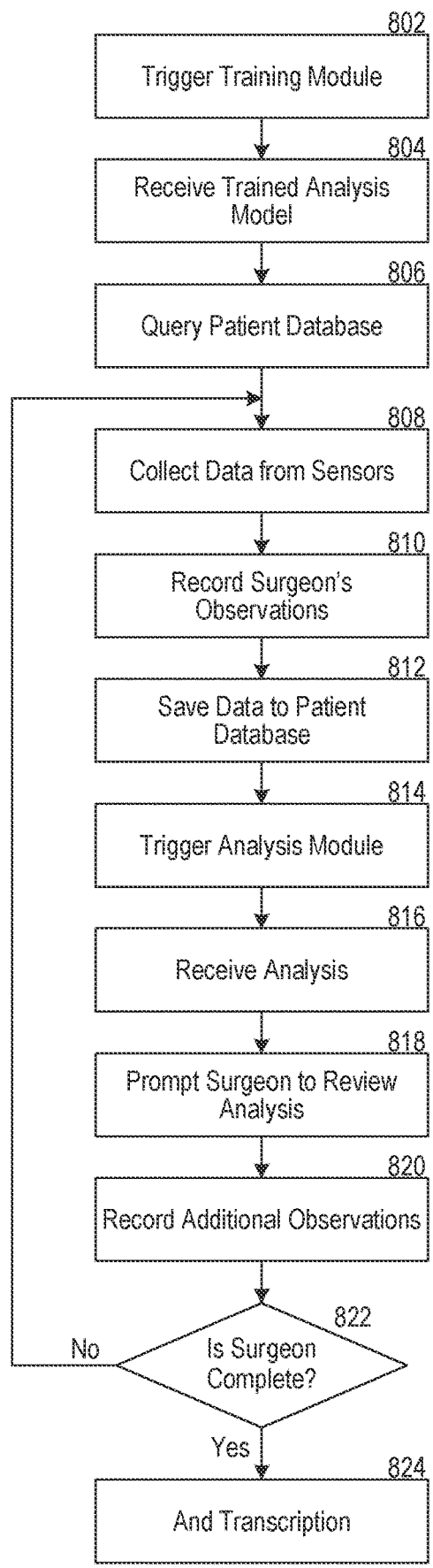
FIG. 8 is a flow diagram illustrating an example process for transcribing and performing analysis on patient data, in accordance with one or more embodiments.

FIG. 8 is a flow diagram illustrating an example process for transcribing and performing analysis on patient data, in accordance with one or more embodiments. In some embodiments, the process of FIG. 8 is performed by the transcription module 626. The transcription module 626 is illustrated and described in more detail with reference to FIG. 6. In other embodiments, the process of FIG. 8 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 802, the transcription module 626 prompts or triggers the training module 628 (see FIG. 6) to train an analysis model. The analysis model may be generalized or domain specific, such as for use by a diagnostic oncologist. The training module 628 queries the patient database 624 for patient data, selecting patient data received during the diagnosis of a medical condition and predicting the patient's diagnosis. The analysis model is then updated based on the results of the prediction and further trained with any additional patient data available.

In step 804, the transcription module 626 receives a trained analysis model from the training module 628. The trained analysis model may be generalized or domain specific. For example, the analysis model is trained using images acquired via an MRI to recognize lung cancer. In a further example, the analysis model is additionally trained using non-image data including vital sign measurements, diagnostic test results, symptoms, patient history, and family medical history. In some embodiments, the transcription module 626 receives one or more trained analysis modules that can include, without limitation, one or more transcription modules and/or condition-specific modules, such as cardiac transcribing models, oncology transcribing models, respiratory transcribing models, or the like. In some embodiments, the transcribing module includes a transcribing model and/or a vocabulary database. The vocabulary database can be a cloud database or a local database. For example, the system can select a cardiac transcribing model with one or more transcription models and a cardiac vocabulary database based on received cardiac-related sensor data, such as heart monitor data, EKGs, or the like. In some embodiments, the system generates a condition-specific module and associated condition vocabulary database if a suitable module is not available.

In step 806, the transcription module 626 queries the patient database 624 for data relevant to the patient. The data includes the patient's medical history including previous vital sign measurements, symptoms and signs of illness noted by a medical professional, previous diagnostic test results, and previous diagnoses. The data may additionally include the patient's family medical history and their genetic information including sequenced DNA which may be used to identify hereditary medical conditions. For example, data is retrieved describing a 39-year-old male patient with a history of smoking cigarettes for 18 years, a prior diagnosis for pneumonia and images from two MRIs taken at a six-month interval.

In step 808, the transcription module 626 collects or retrieves data from one or more sensors 620. The sensors 620 may include any of a pulse oximeter, sphygmomanometer, electrocardiogram, glucometer, etc. The sensors 620 may additionally include one or more imaging devices. Alternatively, the transcription module 626 collects data from a medical professional such as a surgeon, nurse, physician's assistant, paramedic, emergency medical technician, etc. The data may be measured manually and either manually inputted using a physical user interface 610 or may be provided via a verbal interface. For example, a heart rate of 120 beats per minute and a blood oxygen saturation of 94 is measured via a pulse oximeter. A series of images is additionally collected from an MRI of the patient's chest focused on the patient's lungs. The data collected further includes a verbal prompt from a nurse manually measuring the patient's blood pressure and saying, "the patient's blood pressure is 145/95."

In some embodiments, one or more processors of the system of FIG. 6 transcribe speech input received from a surgeon examining a patient into medical notes, including electronic medical notes. The speech input is received via a microphone of the system. For example, in step 810, the transcription module 626 records a surgeon's observations. The surgeon may alternatively be any medical professional or assisting personnel. The observations may be provided manually via a physical user interface 610, such as a keyboard or a touchscreen, or in a preferred embodiment, may be orally dictated by the surgeon or other medical professional. The dictation may further include treatments or interventions which are either being performed or alternatively are instructions for execution by the patient or another medical professional such as a nurse. For example, the surgeon observes the procedure and states, "the patient is experiencing shortness of breath and increased work of breathing," and additionally, "we are providing the patient 3 liters per minute of oxygen via nasal cannula." The surgeon may further dictate observations while reviewing medical records or medical images. For example, the surgeon notes that, "there appears to be a mass on the inferior lobe of the right lung," and further, "schedule a sputum test and additionally a biopsy if the sputum test is positive."

The transcription module 626 can perform, without limitation, Fourier analysis, linear predictive coding, perceptual linear coding, and/or extraction routines and can apply one or more speech recognition algorithms, including hidden Markov Models/algorithms, dynamic time warping, and/or artificial neural networks. The Markov algorithms can include, for example, forward algorithms, Viterbi algorithms, forward-backward algorithms, etc. The transcription module 626 can be trained using supervised learning, unsupervised learning, reinforced learning, or other machine-learning techniques disclosed herein (see FIG. 2) for speech recognition, speech-to-text, etc. In some embodiments, the transcription module 626 transcribes speech input from a physician by converting the speech to text by using, for example, one or more profiles (e.g., practitioner profiles, specialty profiles, or a user profile for the physician). The profiles can be trained using one or more machine learning models trained on speech data sets generated by instructing the users to provide input speech.

In step 812, the transcription module 626 stores or saves the data (including the medical notes) to the patient database 624. The data includes sensor data and the medical notes received via manual or verbal dictation including the surgeon's observations. For example, the data includes a measured heart rate of 120 and a blood oxygen concentration of 94, a blood pressure of 145/95 and further the surgeon's observations of the patient indicating, e.g., shortness of breath, increased work of breathing, and a mass on the inferior lobe of the right lung. The data further includes interventions or instructions. Continuing the example, the data indicates that the patient was provided 3 liters per minute of oxygen via nasal cannula and that the surgeon requested a sputum test and a biopsy pending a positive result from the sputum test.

In some embodiments, one or more processors of the system of FIG. 6 determine a diagnosis for a patient using a machine learning model (see FIG. 2) of the system based on sensor data, patient data, and medical notes. The machine learning model is trained based on historical patient data and historical treatment data (see FIG. 7). In step 814, the transcription module 626 prompts or triggers the analysis module 630 to analyze the patient data. The analysis module 630 receives patient data from the patient's most recent or current assessment and retrieving the patient's medical history from the patient database 624. In some embodiments, the one or more processors generate a treatment for a patient using the machine learning model based on a diagnosis. For example, the analysis module 630 further selects an analysis model and using the analysis model to analyze the patient data for possible diagnoses, observations not made by the surgeon or other medical professional, additional diagnostic tests, or information to collect from the patient, as well as possible treatments and the likelihood of the treatments benefiting the patient. For example, the data provided to the analysis module 630 indicates a measured heart rate of 120 and a blood oxygen concentration of 94, a blood pressure of 145/95 and further the surgeon's observations of the patient indicating shortness of breath, increased work of breathing, and a mass on the inferior lobe of the right lung. The data further includes interventions or instructions. Continuing the example, the data further indicates that the patient was provided 3 liters per minute of oxygen via nasal cannula and that the surgeon requested a sputum test and a biopsy pending a positive result from the sputum test.

The system of FIG. 6 supports voice-interactive natural language dialogue using natural language with the physician to, for example, provide information, obtain information for analyzing the patient, etc. This process can be repeated until a confidence score exceeding a threshold value is achieved. The confidence score indicates the likelihood of an accurate outcome of the analysis based on, for example, historical data or other data. The system of FIG. 6 can identify additional information (e.g., physician observations, patient feedback, etc.) that are useful for analysis. The system can generate computer-generated natural language requests provided via voice-interactive transcription (text-to-voice) requests. The physician can provide the additional information. The system can include any number of machine learning models, transcription modules, diagnostic modules, treatment modules, and/or databases to support the natural language voice interaction.

In some embodiments, step 814 includes selecting a machine learning model from a set of machine learning models based on at least one health parameter for the patient. This allows the system to increase accuracy, reduce computation times, and otherwise improve performance. For example, the machine learning model can be selected based on health status, patient condition, physician-selected health parameter for the patient, or other health parameters. The health status can indicate general health status (e.g., good health, poor health, etc.), impact of disease/condition on a patient, etc. In some embodiments, the health status can be generated based on health-related quality-of-life questionnaires. The patient condition can be, for example, undetermined, good, fair, serious, or critical. The physician-selected health parameter can be indicative of the physician's observations.

In step 816, the transcription module 626 receives an analysis completed by an analysis model. For example, the analysis indicates that the patient has an 80% likelihood of having lung cancer and further identifying a further question to be asked of, "have you had a persistent cough or chest pain?" The analysis may further indicate that radiotherapy would have a 70% likelihood of benefiting the patient while chemotherapy would have only a 60% likelihood of benefiting the patient.

The transcription module 626 can function as a conversational speech synthesis module that produces computer-generated speech based on one or more transcription models. In some embodiments, the system can include or interface with speech or language models from Monkey-Learn™, IBM Watson™, or Google Cloud Natural™ and can include or interface with specific application programming interfaces (APIs) for speech input (e.g., natural language requests). The system can process the inputs to extract one or more elements used to identify one or more associated APIs. One or more structured API calls can be generated by mapping the extracted elements to elements of the structured API calls. The system can communicate with remote servers to construct structured API calls. The communications with the APIs can be selected based on the API capabilities, such as natural language processing or other speech processing modules disclosed herein.

In some embodiments, a user interface of the system of FIG. 6 displays a graphical representation of a generated treatment for viewing by a physician. For example, in step 818, the transcription module 626 prompts the surgeon or other medical professional to review the analysis results returned by the analysis module 630. In some embodiments, the prompt is a notification indicating to a surgeon that the analysis results are available for review via a user interface 610 and/or via an audio interface. In a preferred embodiment, the system provides an interactive natural language dialogue in which a surgeon is prompted by a verbal interface in a conversational manner such as, "the analysis for the patient is complete, would you like to review?" The surgeon may respond by saying, "I will review the results later," or alternatively may reply, "what are the results?" The results may then be presented to the surgeon as, "there is an 80% likelihood that the patient has lung cancer as you identified in your observations. In step 816, the transcription module 626 can prompt the surgeon to, e.g., ask the patient whether he has a persistent cough or has had chest pain to improve the accuracy of the diagnosis." The surgeon may further request a deeper analysis, or the results of an already completed deeper analysis such as by, "how would the patient respond to radiotherapy?" to which the surgeon would be told, "there is a 70% likelihood that radiotherapy would benefit the patient."

In step 820, the transcription module 626 stores or records additional observations or instructions provided by the surgeon or other medical professional. The observations may be in response to the analysis results or may include information acquired by the surgeon since the analysis was completed. The surgeon may additionally provide instructions such as additional tests to be completed or treatments. The observations or instructions may be provided via a traditional user interface 610 or may alternatively be dictated verbally. For example, the surgeon dictates that, "if the results of the sputum test are positive, begin the patient on six weekly sessions of radiotherapy and schedule a follow up appointment one week after the sixth session."

In step 822, the transcription module 626 determines whether a surgical procedure or surgery is complete, by receiving an explicit command from the surgeon, such as the surgeon saying, "end the transcription" or by monitoring the presence of the surgeon and determining a surgery is complete when the surgeon leaves the room. The surgery may be determined to be complete regarding the present patient if the surgeon inquires or otherwise begins a new session with a new patient. If the surgery is not complete, the transcription module 626 retrieves or collects data from sensors if available and continues to collect information, including the surgeon's observations and instructions. In step 824, the transcription module 626 terminates the transcription if the surgeon is complete. Additionally, instructions may be executed following the completion of the transcription such as scheduling follow up appointments or treatments as provided by the surgeon.

Figure 9:
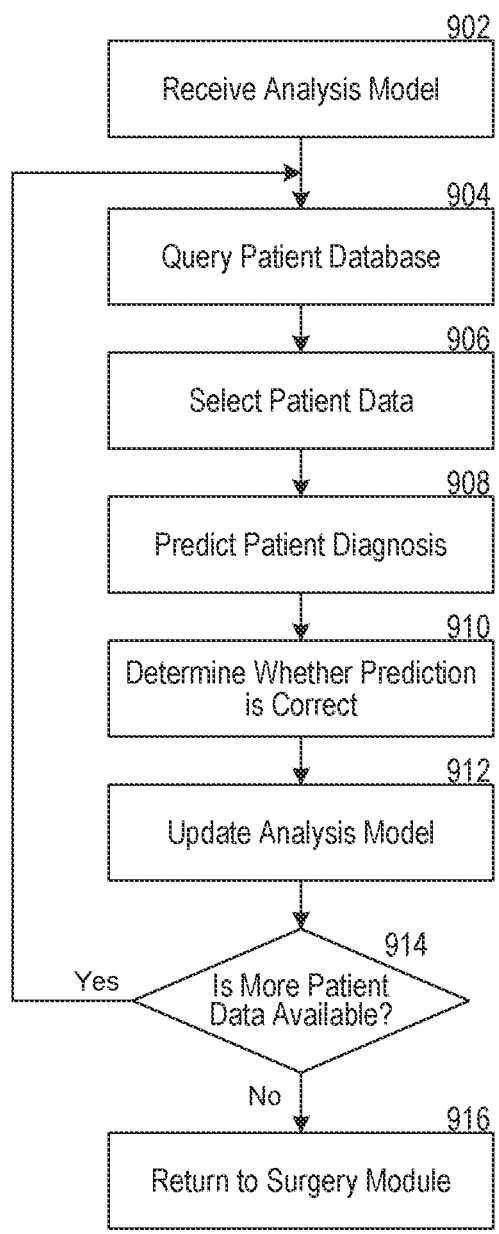
FIG. 9 is a flow diagram illustrating an example process for transcribing and performing analysis on patient data, in accordance with one or more embodiments.

FIG. 9 is a flow diagram illustrating an example process for transcribing and performing analysis on patient data, in accordance with one or more embodiments. In some embodiments, the process of FIG. 9 is performed by the training module 628. The training module 628 is illustrated and described in more detail with reference to FIG. 6. In other embodiments, the process of FIG. 9 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In some embodiments, received sensor data includes medical images of the patient's body, and the one or more sensors 620 include an imaging device 612. One or more processors of the system of FIG. 6 extract an anomalous feature from the medical images. A diagnosis is determined using machine learning (see FIG. 2) performed on the anomalous feature. For example, in step 902, the training module 628 retrieves or receives an analysis model. The analysis model is an artificial intelligence trained using machine learning (see FIG. 2) to analyze past and current patient data to identify insights such as potential questions to ask a patient, possible diagnoses, or identification of the presence of an anomalous feature in medical images taken with an imaging device 612. The analysis model may be generalized, such as which might be used by a physician or other general medical practitioner. Alternatively, the analysis model may be specialized for use by a specialist such as an oncologist, pediatrist, dermatologist, cardiologist, endocrinologist, etc. For example, the analysis model is specialized for use by an oncologist.

In step 904, the training module 628 queries the patient database 624 for patient data. The patient data may be limited, such as by the domain of the analysis model it will be used to train. For example, if the domain is oncology, the data retrieved may be only for those patients who have been diagnosed with a cancer. Similarly, data retrieved may be determined by the area in which the doctor who is going to use it is focused, such as diagnostic, surgical, treatment, etc. The data retrieved for a diagnostic oncologist may be limited to images acquired from an imaging device 612. The data may further include vital sign measurements, symptoms, the patient's medical history, and their family medical history. The data may also include genetic information such as sequenced DNA. In an example, the data includes MRIs from patients who were screened for lung cancer.

In step 906, the training module 628 identifies or selects data for a single patient from the patient data retrieved from the patient database. The data includes the information which was available at the time of the patient's diagnosis. In an example, the patient data includes a series of three MRIs taken at an interval of six months. The data may further include vital sign measurements, symptoms noted by the patient or a medical professional and the patient's prior medical history and family medical history prior to the screening.

In step 908, the training module 628 generates or predicts the patient's diagnosis using the selected patient data. The prediction is made by performing image analysis, such as using a convolutional neural network (CNN) on one or more medical images captured using an imaging device 612. The prediction may additionally or alternatively use non-image data such as vital sign measurements, diagnostic test results, symptoms, patient history, and family medical history.

In some embodiments, determining a diagnosis includes, for each of one or more medical conditions, assigning a statistical probability that a patient has a particular medical condition using a machine learning model (see FIG. 2). The medical condition having the greatest statistical probability is selected. For example, the analysis model assigns a statistical probability that the patient may have a disease or medical condition, and selects the medical condition with the highest probability. In some embodiments, one or more processors of the system of FIG. 6 select each of the one or more medical conditions having a statistical probability greater than a threshold statistical probability. For example, the analysis model assigns a statistical probability that the patient may have a disease or medical condition, and selects one or more illnesses with a probability above a threshold value.

In some embodiments, training a machine learning model (see FIG. 2) includes generating, by one or more processors of the system of FIG. 6, a predicted diagnosis and a predicted treatment for a previous patient based on the historical patient data (see FIG. 7). The one or more processors compare the predicted diagnosis and the predicted treatment to an actual diagnosis and an actual treatment provided by a previous surgeon in the historical patient data. The comparing is performed for training a regression model of the system based on the comparison results. In an example, the analysis model predicts that the patient has an 85% likelihood of having lung cancer based on analysis of the series of three MRIs from the selected patient data. Continuing the example, the threshold value for a positive diagnosis is 70%, as set by a medical professional, therefore the prediction is that the patient was diagnosed with lung cancer. If there are no diseases or medical conditions with a statistical probability above the threshold value, the patient is determined to be healthy. More than one disease or medical condition may be selected as a diagnosis. The prediction may be made for each possible disease or medical condition discretely, each being considered independent of the others, or the likelihood of each disease or medical condition may be considered relative to each of the other possible diagnoses.

In step 910, the training module 628 determines whether the prediction is correct by retrieving the patient's actual diagnosis from the patient database 624 and comparing the patient's actual diagnosis to the predicted diagnosis. If the predicted diagnosis matches the actual diagnosis, then the prediction is correct. In an example, the patient's actual diagnosis is lung cancer, which is the same as the predicted diagnosis, therefore the prediction is correct. In an alternate example, the actual diagnosis is a pulmonary embolism, which is different than the predicted diagnosis of lung cancer, therefore the prediction is incorrect. If multiple diagnoses were predicted, then each may be considered for correctness independently from the others predicted.

In step 912, the training module 628 updates the analysis model based upon the results of the prediction. The analysis model may be updated using a regression model, such that a correct prediction reinforces the current model while an incorrect prediction results in an adjustment made to the model. In step 914, the training module 628 determines or checks whether there is more patient data which has not yet been used to train the analysis model, and if so, queries the patient database 624 for additional data. In an example, there is data on another patient who was screened for lung cancer, therefore there is more patient data available. In an alternate example there is no more patient data for patients screened for lung cancer. In step 916, the training module 628 returns control to the transcription module 626 if there is no additional data to train the analysis model.

Figure 10:
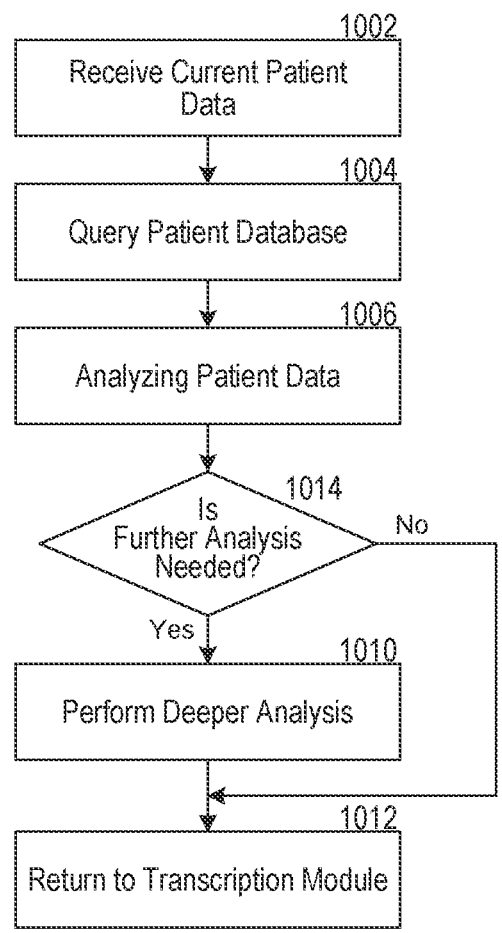
FIG. 10 is a flow diagram illustrating an example process for transcribing and performing analysis on patient data, in accordance with one or more embodiments.

FIG. 10 is a flow diagram illustrating an example process for transcribing and performing analysis on patient data, in accordance with one or more embodiments. In some embodiments, the process of FIG. 10 is performed by the analysis module 630. The analysis module 630 is illustrated and described in more detail with reference to FIG. 6. In other embodiments, the process of FIG. 10 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1002, the analysis module 630 receives patient data from the patient's current visit. The data includes sensor data and data received via manual or verbal dictation including the surgeon's observations. In an example, the data includes a measured heart rate of 120, a blood oxygen concentration of 94, a blood pressure of 145/95, and further includes the surgeon's observations of the patient including shortness of breath, increased work of breathing, and a mass on the inferior lobe of the right lung. The data further specifies interventions or instructions. Continuing the example, the data can further indicate that the patient was provided 3 liters per minute of oxygen via nasal cannula and that the surgeon requested a sputum test and a biopsy pending a positive result from the sputum test.

In some embodiments, patient data includes sequenced DNA of a patient and a diagnosis includes a hereditary medical condition. For example, in step 1004, the analysis module 630 queries the patient database 624 for the patient's medical history and family medical history. The data includes the patient's medical history including previous vital sign measurements, symptoms and signs of illness noted by a medical professional, previous diagnostic test results, and previous diagnoses. The data may additionally include the patient's family medical history and their genetic information including sequenced DNA which may be used to identify hereditary medical conditions. The patient database 624 may further be queried for a suitable analysis model for analyzing the patient's past medical history and observations made during the patient's most recent or current assessment. In an example, the analysis module 630 retrieves data describing a 39-year-old male patient with a history of smoking cigarettes for 18 years, a prior diagnosis for pneumonia, and images from two MRIs taken at a six-month interval.

In step 1006, the analysis module 630 analyzes the patient's data including both the patient's medical history retrieved from the patient database 624 and the most recently acquired information from the patient's most recent or current assessment. The analysis module 630 identifies diagnoses with a high likelihood given the provided information. Additionally, the analysis module 630 identifies missing information which may either confirm or eliminate a possible diagnosis. In an example, the analysis model determines that the patient has an 80% likelihood of having lung cancer. Further, the analysis module 630 generates or suggests a question for the surgeon or other medical professional to ask the patient, "have you had a persistent cough or chest pain?"

In step 1008, the analysis module 630 determines whether further analysis is needed. Further analysis is required if the analysis is inconclusive or if indicated by the surgeon or other medical professional. A deeper analysis may also be required based upon the information available for analysis. Some image analysis, such as video, may require greater computational capabilities. Similarly, a pathology study may require more resources for genetic sequencing or advanced simulation of a disease's potential progression. Further analysis may also be required for treatments proposed either by a surgeon, other medical professional, or an assessment model to assess whether a treatment is likely to be effective or alternatively to identify an effective treatment. In an example, the patient is suspected of having lung cancer and both radiotherapy and chemotherapy are recommended treatments and further analysis is required to simulate the likely effectiveness of the treatments.

In some embodiments, one or more processors of the system of FIG. 7 simulates (see FIGS. 4A-5) an effectiveness of a treatment on a patient's body based on a diagnosis, sensor data, the patient data, and medical notes. A user interface displays results of the simulation for viewing by a physician. For example, in step 1010, the analysis module 630 performs a deeper analysis of the patient data using alternate analysis models or more powerful computational resources such as cloud computing, a supercomputer, or a quantum computer. The more capable resources enable a more detailed analysis of the patient data in a timely manner. For example, the analysis module 630 simulates the effectiveness of radiotherapy and chemotherapy as treatments for the patient's likely diagnosis of lung cancer and determines that radiotherapy would have a 70% likelihood of benefiting the patient while chemotherapy would have a 40-60% likelihood of benefiting the patient depending on the mixture of drugs. Additionally, the analysis module 630 reassesses and confirms the initial 80% likelihood of a lung cancer diagnosis.

In step 1012, the analysis module 630 returns control to the transcription module 626 with the analysis completed by an analysis model. In an example, the analysis indicates that the patient has an 80% likelihood of having lung cancer and generates or identifies a further question to be asked of, "have you had a persistent cough or chest pain?" The analysis may further include that radiotherapy would have a 70% likelihood of benefiting the patient while chemotherapy would have only a 60% likelihood of benefiting the patient.

The functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments. The methods and steps discussed in connection with FIGS. 8-10 can be performed using the systems and components discussed in connection with FIGS. 1-6. For example, the console 108 of FIG. 1 can include one or more microphones for receiving voice input from an individual, the database 106 of FIG. 1 can include any databases disclosed herein, and the operating room 102 of FIG. 1 can include the systems and components discussed in connection with FIGS. 4A-10.

The machine learning system 200 of FIG. 2 can be used for transcribing, diagnosing, treatment planning, or other actions disclosed herein. For example, the machine learning model discussed in FIG. 2 can be trained using voice training data. A diagnostic machine learning model can be trained using diagnostic training data. A treatment planning machine learning model can be trained using treatment training data. The data sets can be obtained by the healthcare provider, from a remote database (e.g., database 108 of FIG. 1), or other source. In some embodiments, simulations can be performed to generate additional data sets.

The systems disclosed herein can also determine whether to train a machine learning model. This allows further training to increase accuracy. For example, if a confidence score for a trained machine learning model is below a threshold value, the system can determine a training protocol to further train the machine learning system or transition to a different machine learning system. In some training protocols, the system identifies a training database based on the patient data. The system can match the patient data with training sets in available databases. The system can then train the machine learning model using the matched training data. If the surgeon determines that the received analysis at a step (e.g., steps 816, 818, 906) is inaccurate, the surgeon can provide additional information to the system. The surgeon can request re-training the machine learning model to re-train the previously used machine learning model or to use another machine learning model. Additional training of machine learning models can also be performed at steps discussed in connection with of FIGS. 8-10.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

What is claimed is:

1. A method comprising:
   generating, by a computer system, sensor data using one or more sensors associated with a patient's body;
   retrieving, by the computer system, patient data of the patient from a patient database, the patient data comprising at least a medical history of the patient;
   performing, by the computer system, a computer-generated interactive conversation between the computer system and a physician using a user interface to generate speech input, wherein the user interface comprises a microphone and the physician is examining the patient;
   transcribing, by the computer system, the speech input received via the microphone from the physician into medical notes;
   determining, by the computer system, a diagnosis for the patient using a machine learning model based on the sensor data, the patient data, and the medical notes, wherein the machine learning model is trained based on historical patient data and historical treatment data; and
   outputting, by the computer system, computer-generated speech to provide the diagnosis to the physician using a user interface.

2. The method of claim 1, further comprising generating, by the computer system, the computer-generated speech using a conversational speech synthesis module, wherein the computer-generated speech describes a treatment associated with the diagnosis.

3. The method of claim 1, further comprising generating, by the computer system, computer-generated conversational speech describing one or more analyses of the patient data associated with the diagnosis.

4. The method of claim 1, further comprising using, by the computer system, one or more machine learning models trained using conversation training sets for the computer-generated speech and/or voice recognition.

5. The method of claim 1, further comprising:
   generating, by the computer system, a treatment for the patient using the machine learning model trained on a diagnosis training set; and
   presenting, by the computer system, the treatment to the physician using the user interface.

6. The method of claim 1, wherein the sensor data comprises medical images of the patient's body and the one or more sensors comprise an imaging device, the method further comprising:
   extracting, by the computer system, an anomalous feature from the medical images, wherein the diagnosis is determined using machine learning performed on the anomalous feature.

7. The method of claim 1, wherein determining the diagnosis comprises:
   for each of one or more medical conditions:
      assigning, by the computer system, a statistical probability that the patient has each medical condition using the machine learning model; and
   selecting, by the computer system, a medical condition having a greatest statistical probability.

8. The method of claim 7, further comprising:
   selecting, by the computer system, each of the one or more medical conditions having a statistical probability greater than a threshold statistical probability.

9. The method of claim 1, wherein training the machine learning model comprises:
   generating, by the computer system, a predicted diagnosis and a predicted treatment for a previous patient based on the historical patient data; and
   comparing, by the computer system, the predicted diagnosis and the predicted treatment to an actual diagnosis and an actual treatment provided by a previous surgeon in the historical patient data, the comparing for training a regression model.

10. The method of claim 1, wherein the patient data comprises sequenced DNA of the patient, and the diagnosis comprises a hereditary medical condition.

11. The method of claim 1, further comprising:
   simulating, by the computer system, an effectiveness of the treatment on the patient's body based on the diagnosis, the sensor data, the patient data, and the medical notes; and
   displaying, by the computer system, results of the simulation using the user interface for viewing by the physician.

12. A system comprising:
   one or more computer processors; and
   a non-transitory computer-readable storage medium storing computer instructions, which when executed by the one or more computer processors, cause the system to:
      generate sensor data using one or more sensors associated with a patient's body;
      transcribe speech input received via a microphone of the computer system from a physician into medical notes, wherein the physician is examining the patient;
      determine a diagnosis for the patient using a machine learning model based on the sensor data, the patient data, and the medical notes, wherein the machine learning model is trained based on historical patient data and historical treatment data; and
      output computer-generated speech to provide the diagnosis to the physician using a user interface.

13. The system of claim 12, wherein the sensor data comprises medical images of the patient's body and the one or more sensors comprise an imaging device, the computer instructions further causing the system to:

extract an anomalous feature from the medical images, wherein the diagnosis is determined using machine learning performed on the anomalous feature.

14. The system of claim 12, wherein the computer instructions to determine the diagnosis cause the system to:
for each of one or more medical conditions,
assign a statistical probability that the patient has each medical condition using the machine learning model; and
select a medical condition having a greatest statistical probability.

15. The system of claim 14, wherein the computer instructions further cause the system to:
select each of the one or more medical conditions having a statistical probability greater than a threshold statistical probability.

16. The system of claim 12, wherein the computer instructions to train the machine learning model cause the system to:
generate a predicted diagnosis and a predicted treatment for a previous patient based on the historical patient data; and
compare the predicted diagnosis and the predicted treatment to an actual diagnosis and an actual treatment provided by a previous surgeon in the historical patient data to train a regression model of the system.

17. The system of claim 12, wherein the patient data comprises sequenced DNA of the patient, and the diagnosis comprises a hereditary medical condition.

18. The system of claim 12, wherein the computer instructions further cause the system to:
simulate an effectiveness of the treatment on the patient's body based on the diagnosis, the sensor data, and the medical notes; and
display results of the simulation using the user interface for viewing by the physician.

19. The system of claim 12, wherein the computer instructions further cause the system to:
retrieve patient data of the patient from a patient database, the patient data comprising at least a medical history of the patient, and wherein the diagnosis and the treatment are generated based further on the patient data.

* * * * *